United States Patent [19]

Marks

[11] 3,948,636
[45] Apr. 6, 1976

[54] FLOWABLE AQUEOUS COMPOSITION OF WATER-INSOLUBLE PESTICIDE

[75] Inventor: Alfred F. Marks, Mentor, Ohio

[73] Assignee: Diamond Shamrock Corporation, Cleveland, Ohio

[22] Filed: Nov. 9, 1972

[21] Appl. No.: 305,064

[52] U.S. Cl. .......................... 71/112; 71/67; 71/79; 71/105; 71/DIG. 1; 424/300; 424/304; 424/363
[51] Int. Cl.² .......................................... A01N 9/24
[58] Field of Search .......... 71/79, 105, 112, DIG. 1; 424/300, 304, 363

[56] References Cited
UNITED STATES PATENTS

| | | | |
|---|---|---|---|
| 3,484,229 | 12/1969 | Floyd et al. | 71/79 X |
| 3,551,133 | 12/1970 | Sprayberry et al. | 71/79 |
| 3,594,151 | 7/1971 | Sprayberry et al. | 71/79 |
| 3,717,452 | 2/1973 | Gibsen et al. | 71/79 |

Primary Examiner—Glennon H. Hollrah
Attorney, Agent, or Firm—Helen P. Brush

[57] ABSTRACT

An easily handled, flowable, pesticide composition contains as essential components in water as the sole liquid medium, from 10 to 60%, by weight, of at least one solid, substantially water-insoluble pesticidally-active ingredient; from 1 to 10%, by weight, of a water-soluble nonionic surfactant; and from 0.02 to 1% by weight of a heteropolysaccharide gum. Optional ingredients of the composition include, for example, antifoam agents, anticaking agents, and freeze-point depressants. This composition is an extremely stable suspension. It is totally dispersible in water, providing agglomerate-free pesticidal spray compositions.

15 Claims, No Drawings

FLOWABLE AQUEOUS COMPOSITION OF WATER-INSOLUBLE PESTICIDE

BACKGROUND OF THE INVENTION

Many pesticides including herbicides, fungicides, insecticides, nematocides, etc., are practically insoluble in water and oftentimes may be sparingly soluble in petroleum hydrocarbons, which liquids are both convenient and inexpensive as carriers for providing easily applied pesticide formulations. Because of their insoluble nature, various methods thus have been devised heretofore for applying these pesticidally-active ingredients onto the substrate to be protected. Conventionally, such pesticides have long been applied in rather dilute compositions containing a low percentage of active ingredient. As handling of these dilute compositions and their transport to the point of use is both burdensome and expensive, various improved formulations have been developed which contain insoluble pesticides in concentrated form. Such formulations include, e.g., wettable powders, dust concentrates, aqueous suspensions, and oil/water suspensions.

Wettable powders consist of the active ingredient mixed with a suitable solid carrier and may also contain a surfactant or dispersant. For application, the wettable powder is measured out in certain proportions, is diluted with water, and then stirred to form a suspension. Use of a wettable powder is disadvantageous in that it is somewhat difficult to handle when preparing the suspensions. Further, it has a tendency to cake during storage prior to contact with water, and can be extremely sensitive to high temperatures.

Water-in-oil suspensions wherein the oil is a continuous phase usually are very thick pastes. These are not easily flowable and dispersible in water. Also, they oftentimes may be unstable during storage due to changes in the crystal structure of the pesticide which promote its settling and agglomeration.

Aqueous suspensions of insoluble pesticides heretofore typically have contained only low concentrations of pesticide together with numerous adjuvants for promoting storage stability in the formulation by preventing undue caking and/or agglomeration of the pesticidal component. These suspensions, however, have not consistently possessed good water dispersibility, nor has settling or caking or the pesticide been adequately prevented.

There has long been a need in the art for a flowable aqueous pesticide composition which is easily handled during preparation and use, which has excellent shelf-life even during extended storage and which is completely dispersible in water. Particularly, a flowable, storage-stable and water-dispersible composition which can contain a high concentration of pesticide component, e.g., up to and including about 6 lbs pesticide per gallon of formulation, has long been desired.

The present invention comprises a liquid, easily flowable pesticide composition completely dispersible in water comprising an aqueous suspension of at least one solid, essentially water-insoluble pesticidally-active component, which composition is characterized by excellent storage stability. In addition to the homogeneously dispersed pesticidally-active ingredient, this composition contains a minor quantity each of a heteropolysaccharide gum and at least one nonionic surfactant, and optionally other adjuvants such as anticaking agents, antifoam agents, freeze-thaw depressants, and the like. Most significantly, it retains its outstanding stability and dispersibility characteristics even when incorporating extremely high solids concentration, e.g., up to and including 6 lbs of pesticide per gallon.

DESCRIPTION OF PREFERRED EMBODIMENTS

As previously set forth herein, the flowable pesticidal composition of this invention comprises an aqueous homogeneous suspension of at least one solid pesticidal ingredient, water solely being employed as the liquid suspending medium.

This composition generally may contain, by weight,
1. 10–60% of at least one finely-divided, essentially water-insoluble pesticide;
2. 1–10% of a nonionic surfactant;
3. 0.02–1.0% of a heteropolysaccharide gum;
4. 0–10% of an anticaking agent;
5. 0–5%, by weight of an antifoaming agent; and
6. 0–10% of a freeze-point dispersant, with water being used in sufficient quantity to provide, in combination with the other ingredients, 100 parts of finished composition. Depending upon the specific storage and use conditions for any particular composition, as will be discussed more fully hereinafter, adjuvants such as freeze-point depressants, anticaking agents, and antifoaming agents are advantageously incorporated into the composition.

As used herein in the specification and claims, the terms "active," "pesticidally-active," "pesticide," "pesticidal," and the like, are each intended to refer to toxicants and to biological compositions containing these chemicals which are effective in killing, preventing, or controlling the growth of undesirable pests, i.e., plants, insects, mice, microorganisms, algae, fungi, bacteria, and the like, said chemicals and compositions being commonly known, e.g., as insecticides, miticides, bactericides, algacides, fungicides, nematocides, herbicides, etc. The toxicant chemicals employed in the flowable pesticide formulations of this invention are essentially insoluble in water, that is to say, they are typically less than 1% soluble in water. Exemplary of specific toxicant compounds known and used heretofore as pesticides which suitably may be employed as such in the composition of this invention include the following:

DDT (dichloro diphenyl trichloroethane)
2,4-D (2,4-dichlorophenoxyacetic acid)
2,4,5-T (2,4,5-trichlorophenoxyacetic acid)
Dieldrin (1,2,3,4,10,10-hexachloro-exo-6,7-epoxy-1,4,4a,5,6,7,8,8a-octahydro-1,4-endo, exo-5,8-dimethanonaphthalene)
Atrazine (2-chloro-4-ethylamino-6-isopropylamine-s-triazine)
Endrin (hexachloroepoxyoctahydro-endo,endo-dimethanonaphthalene)
Heptachlor (1,4,5,6,7,8,8-heptachloro-3a,4,7,7a-tetrahydro-4,7-methanoindane)
Ovex (p-chlorophenyl p-chlorobenzenesulfonate)
Lindane (gamma isomer of 1,2,3,4,5,6-hexachlorocyclohexane)
DACTHAL (dimethyl ester of tetrachloroterephthalic acid)
LASSO [2,2-chloro-2',6'-diethyl-N-(methoxymethyl)acetanilide]
Simazine [2-chloro-4,6-bis(ethylamino)-s-triazine]
Monuron [3-(p-chlorophenyl)-1,1-dimethylurea]
Diuron [3-(3,4-dichlorophenyl)-1,1-dimethylurea]

SIRMATE (3,4- and 2,3-dichlorobenzyl-N-methyl-carbamate)
Benefin (N-butyl-N-ethyl-a,a,a-trifluoro-2,6-dinitro-p-toluidine)
BAYER 73 (5,2'-dichloro-4'-nitrosalicylanilide, ethanolamine salt)
Captan [cis-N-(trichloromethylthio)-4-cyclohexane-1,2-dicarboximide]
SEVIN (N-methyl-1-naphthylcarbamate)
DACONIL 2787 (tetrachloroisophthalonitrile)
DEMOSAN (1,4-dichloro-2,5-dimethoxybenzene)
Neburon [1-m-butyl-3-(3,4-dichlorophenyl)-1-methylurea]
Linuron [3-(3,4-dichlorophenyl)-1-methoxy-1-methylurea]
Siduron [1-(2-methylcyclohexyl)-3-phenylurea]
RAMROD (2-chloro-N-isopropylacetanilide)
Prometryne [2,4-bis(isopropylamino)-6-methylmercapto-s-triazine]
Bromacil (5-bromo-3-sec-butyl-6-methyluracil)
Thiram (tetramethylthiuram disulfide)
Ziram (zinc dimethyldithiocarbamate)

In general, the pesticide content of the flowable compositions of this invention may vary from about 10 to 60%, by weight. In those compositions containing high solids content, the pesticide content typically varies from about 40 to 60%, by weight. In practice, the pesticide is employed in a finely-divided form having an average particle size ranging preferably between about 1 to 10 microns. It is desirable that the pesticide materials have an average particle size within the stated range so that the greatest pesticide surface per unit area will be provided, thereby allowing the pesticide to be most homogeneously suspended. Likewise, pesticides which are extremely finely-divided provide per unit area greater biological activity. In preparing the pesticide compositions of this invention, in order to assure that the pesticide ingredient will have the desired average particle size, it may sometimes be necessary to subject the pesticide to airmilling, hammer milling, ball milling, or other conventional comminuting treatment known in the art.

In usual practice herein, compositions of the invention will contain either one or a combination of solid, essentially water-insoluble pesticide components. It is to be noted, however, that it is also possible to prepare suitable compositions which incorporate, in addition to at least one of the aforedescribed pesticides, one or more solid, water-soluble pesticide components. In these compositions, the soluble pesticide will of course be in solution in water as the continuous phase.

The heteropolysaccharide gum and the nonionic surfactant, in combination, comprise the dispersing-suspending system of the flowable pesticide composition of this invention. It is critical to employ these components in certain prescribed ratios both in relation to each other and to the concentration of pesticide component in order to obtain compositions with the desired storage stability and water-dispersibility.

The terms "heteropolysaccharide" and "heteropolysaccharide gum" as used herein are meant to include the use of the polysaccharide in the form of the colloid and its salts, e.g., amine derivatives prepared by the method disclosed, for example, in U.S. Pat. No. 3,244,695.

The heteropolysaccharide which is commonly designated in the art as a xanthan gum, is a high molecular weight linear exocellular material prepared by the action of bacteria of the genus Xanthomonas on carbohydrates. It has a molecular weight in excess of 200,000, preferably over 1 million. A variety of carbohydrates can be fermented with various species of the genus Xanthomonas to produce the heteropolysaccharide. Examples of suitable bacterium species of the genus Xanthomonas include X. campestris, X. carotate, X. inconue, X. begoniae, X. malvacerum, X. vesicatoria, X. translucens, and X. vasculorum, among others. Suitable carbohydrates include, e.g., glucose, sucrose, fructose, maltose, lactose, galactose, soluble starch, corn starch, potato starch, and the like. Preparation of heteropolysaccharides suitably used herein is described in greater detail but not solely in U.S. Pat. No. 3,020,206. It is to be understood that neither the heteropolysaccharides per se nor their preparation constitute a part of the present invention.

In general, any nonionic surfactant which has a suitable hydrophilic-lyophilic balance may be employed in the suspending-dispersing system of the flowable composition of this invention. Specific suitable surfactants are selected from the following classes or types of nonionic surfactant materials: ethoxylated alkylphenols (also designated in the art as alkylaryl polyether alcohols); ethoxylated aliphatic alcohols (or alkyl polyether alcohols); ethoxylated fatty acids (or polyoxyethylene fatty acid esters); ethoxylated anhydrosorbitol esters (or polyoxyethylenesorbitan fatty acid esters); and ethoxylated polyoxypropylene glycols (polyalkylene oxide block copolymers).

Of these, the preferred surfactants at present are the ethoxylated alkylphenols, i.e., alkylaryl polyether alcohols of the general formula:

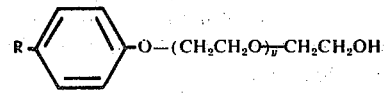

wherein $R = a$ $C_8$-$C_{12}$ linear or branch-chained alkyl group and $y =$ an integer of 8–30, as formulations with both optimum waterdispersibility and adequate storage stability are obtained by using these surfactants. Within this class, especially preferred are those alkylaryl polyether alcohols wherein R is a $C_9$ or $C_{10}$ alkyl group and $y$ is an integer of 9–15.

In practice of the invention, any of the aforedescribed nonionic surfactant compounds generally may be employed as the sole surfactant in the composition, or two or more of these compounds may be employed in combination. Likewise, a portion of any of these compounds, designated herein as primary surfactants, suitably may be replaced by an equivalent quantity of a nonionic surfactant such as, e.g., a liquid lower alkylene glycol ester of a fatty acid, as a secondary surfactant.

The heteropolysaccharide, i.e., xanthan gum, is employed in the composition generally in an amount ranging between 0.02 and 1.0 parts per 100 parts of total formulation while from 1 to 10 parts of the nonionic surfactant moiety generally is incorporated, per 100 parts of the formulation. In compositions of high pesticide solids content, the xanthan gum generally is employed in an amount ranging from 0.1 to 0.5 parts, and the surfactant in an amount ranging generally from 2 to 7 parts, per 100 parts of formulation. If each of these components is employed separately as the sole suspending or dispersing agent in otherwise similar formulations, the solid pesticide component will soon settle out of the continuous water phase. Depending upon the length of time such compositions are then allowed to stand after solids settling, it oftentimes becomes extremely difficult to resuspend the solids therein, even with vigorous and prolonged agitation.

In the pesticide composition of this invention, it is necessary to employ both the heteropolysaccharide and surfactant components within the ranges stated above in order to obtain the desired composition. Formulations containing amounts of these components outside these ranges will either be too thin or too thick and nonflowable, exhibiting inferior water dispersibility.

In practice, viscosities of the prepared compositions may be employed as a general rule to determine whether or not they will possess the desired storage stability and dispersibility in water. Compositions having viscosities ranging from about 8,000 to 30,000 cps, as measured with a Brookfield Viscometer, Model RVT (No. 2 spindle - 0.5 RPM), generally will exhibit the desired characteristics.

Water is present in varying amounts depending upon the quantities employed of the other ingredients, always being present in sufficient quantity to serve as the continuous phase for the dispersed pesticide component and to provide, in combination with the other ingredients, 100 parts of finished formulation. In the preferred compositions, i.e., those which incorporate high concentrations of pesticide, from about 30 to about 40 parts water will generally be employed per 100 parts of finished formulation.

As described previously herein, minor quantities of one or more components such as antifoaming agents, anticaking agents, and freeze-point depressants are incorporated into the composition if it is to be stored for any extended period of time prior to use, particularly under adverse storage conditions. The various, commercially available silicone emulsions are examples of suitable antifoaming agents which may be incorporated in amounts ranging generally from 0.1 to 5.0 parts per 100 parts of the total composition.

Several different types of finely-divided silicas now known in the art are examples of particularly suitable anticaking agents. If employed, from 0.2 to 10 parts of such materials per each 100 parts of the total composition will generally serve to maintain, in combination with the suspending-dispersing system, the desired storage stability of the composition under the most extreme storage conditions. It is particularly advantageous to incorporate anticaking materials into those compositions of high pesticide content.

Lower alkylene glycols, e.g., ethylene or propylene glycol, are examples of suitable freeze-point depressants which are used if the composition is likely to be stored under subtemperate climatic conditions. Amounts of these compounds ranging from about 1 to about 10 parts, per each 100 parts of total composition will adequately provide the composition with the desired antifreeze protection.

To prepare the composition, the order of adding the ingredients is not especially critical, although it is preferred to admix the heteropolysaccharide, surfactant, and any optional components to be incorporated thoroughly in the continuous water phase prior to adding the solid pesticide component or components. Preparation of the composition may be carried out at ambient temperature with mild agitation, no application of heat or undue pressure normally being needed to obtain the desired homogeneous, flowable suspension. However, further mixing of the composition may be carried out employing conventional homogenizing devices, if desired or deemed advisable to assure the most homogeneous suspension of the pesticide component.

The composition of this invention, even if containing a high concentration of pesticide, provides to the routineer an easily flowable formulation which utilizes water as the sole, inexpensive dispersion medium. This composition has excellent bloom characteristics, i.e., it is totally dispersible when added to water. It can be diluted with water in all proportions to provide agglomerate-free, sprayable pesticide compositions of any desired toxicant concentration. Preparation of the spray formulation may be easily accomplished at the application site by simply pouring an appropriate amount of the concentrated composition into water within the spray tank or other convenient container. It is also possible to apply the composition in undiluted form, utilizing newer, specialized spray techniques.

The sprayable, agglomerate-free pesticide compositions formulated from the composition of this invention may be applied from all types of presently used spray equipment with no plugging of the spray nozzles or other malfunction of the spray equipment.

For a fuller understanding of the nature of the invention and the methods for carrying it out, the following illustrative examples are given. In these examples and elsewhere herein, where quantities of ingredients may be given in parts, such proportions are by weight, unless otherwise indicated.

EXAMPLE 1

As an illustration of the invention, 5.2 parts of a nonionic surfactant comprising a polyoxyethylene ether of t-octyl phenol having about 9–10 moles of ethylene oxide per mole of surfactant is dissolved in 38.7 parts of water at ambient temperature. To this solution is added 0.10 part of a heteropolysaccharide with agitation. The heteropolysaccharide gum employed is Kelzan manufactured by the Kelco Company, San Diego, California. Prepared from the bacteria species $X.\ campestris$, this heteropolysaccharide is linear in structure and has a molecular weight greater than 1,000,000. It is composed of recurring units of D-glucose, D-mannose, and D-glucuronic acid in a ratio of 2.8:3.0:2.0.

With continued agitation, 56 parts of tetrachloroisophthalonitrile (DACONIL 2787 fungicide, manufactured by Diamond Shamrock Corporation, Cleveland, Ohio) is incorporated into the prepared suspending agent-surfactant solution. The resulting opaque formulation, grayish in color, is of quite thin consistency and pours easily. However, no phase separation or solids settling is evident in the formulation after it has remained undisturbed for several hours.

A portion of the formulation is poured into a large volume of water. It exhibits excellent bloom, i.e., it disperses completely throughout the water, providing a homogeneous, though diluted formulation.

With continued storage, a very small amount of solids are observed to settle in the formulation after several days. These are easily resuspended with minimum agitation. A sample of the formulation is again poured into water, exhibiting excellent bloom.

For comparison, two other formulations are similarly prepared except that the surfactant is excluded from one of these, and the heteropolysaccharide from the other. In contrast to the homogeneous stable composition described above, each of these formulations is unsatisfactory. That containing no surfactant is a mixture wherein the pesticide solids have not become wetted and dispersed in the water, remaining as a separate phase. In the formulation which contains the surfactant but no suspending agent, the pesticide solids are wetted and dispersed in the water, forming an apparent homogeneous suspension. After preparation, however, this formulation quickly separates into two phases, the solids settling completely out of suspension as a cake-like mass in the bottom of the container. This solids cake cannot be broken up easily and resuspended in the aqueous phase.

EXAMPLE 2

A flowable pesticide composition is prepared from the following formulation:

|  | % by wt |
|---|---|
| Tetrachloroisophthalonitrile | 54.00 |
| Alkylaryl polyether alcohol[1] | 5.20 |
| Heteropolysaccharide gum | 0.10 |
| Propylene glycol | 3.70 |
| Cab-O-Sil M-5[2] | 1.50 |
| Antifoam FG-10[3] | 0.25 |
| Water | 35.25 |

[1]TRITON X-100 - t-octylphenoxy ethoxylated ethanol (9-10 moles ethylene oxide per mole of surfactant) - Rohm and Haas Co.
[2]Submicroscopic anhydrous SiO$_2$ - Cabot Corp.
[3]Silicone emulsion - Dow Corning Corp.

The ingredients of the composition other than the pesticide component are incorporated into the water at ambient temperature after which the pesticide is added. The resulting opaque suspension has a specific gravity of 1.34 g/cc and contains 6 lbs of active ingredient per gallon. It has a Brookfield viscosity of 29,600 cps.

When poured into water, it disperses completely with no evidence of any floc or agglomerate formation.

After being stored for 7 weeks at 50°C, the composition is still a homogeneous suspension, containing no separated solids.

EXAMPLES 3-8

These examples illustrate flowable pesticide compositions according to the invention which incorporate, as the surfactant material, alkylaryl polyether alcohols, i.e., ethoxylated alkylphenols containing different concentrations of ethylene oxide per mole. The general formulation employed is the same as in Example 2, except that 1.0 parts of Hi-Sil 233 (precipitated, hydrated SiO$_2$, manufactured by PPG Chem.) is substituted for the Cab-O-Sil. Also, in each example, 0.15%, by weight of the formulation, of a secondary surfactant material, Nopco Soap "L", is employed along with 5.20% of the primary surfactant. Viscosities of the formulations are measured with a Brookfield viscometer, Model LV, using the No. 3 spindle at 60 RPM.

| Example | Primary Surfactant | Moles Ethylene Oxide | Formulation Viscosity - cps |
|---|---|---|---|
| 3 | Nonylphenoxypoly-(ethyleneoxy)ethanol | 10.5 | 12,140 |
| 4 | " | 15 | 12,640 |
| 5 | Octylphenoxypoly-(ethyleneoxy)ethanol | 10 | 10,600 |
| 6 | " | 12 - 13 | 10,480 |
| 7 | " | 16 | 9,880 |
| 8 | " | 30 | 10,500 |

Each of these formulations which incorporates 6 lbs of active ingredient per gallon, exhibits excellent bloom, i.e., it is completely dispersible in water, with no floc or solids settling developing.

After extended storage at 50°C, each formulation is found to contain no agglomerated solids layer. A minimal water layer is observed at the top of each sample which can be readily remixed with gentle swirling of the formulation.

EXAMPLE 9

A flowable herbicide composition is prepared as previously described using the following formulation:

|  | % by wt |
|---|---|
| Dimethyl ester of tetrachloro-terephthalic acid | 55.70 |
| Ethoxylated polyoxypropylene glycol[1] | 5.20 |
| Heteropolysaccharide | 0.10 |
| Propylene glycol | 3.70 |
| Hi-Sil 233 | 1.00 |
| Antifoam FG-10 | 0.25 |
| Water | 34.00 |

[1]PLURONIC P-104 - BASF Wayandotte Corp.

This composition has the same excellent bloom characteristics and storage stability as the compositions of the previous examples.

EXAMPLE 10

A fungicide composition is prepared from the following formulation:

|  | % by wt |
|---|---|
| Tetrachloroisophthalonitrile | 40.0 |
| Hyonic PE 100[1] | 3.00 |
| Heteropolysaccharide | 0.30 |
| Ethylene glycol | 5.00 |
| Hi-Sil 233 | 1.00 |
| Antifoam FG-10 | 0.25 |
| Water | 50.50 |

[1]alkylphenoxypoly(etheneoxy)ethanol surfactant - Diamond Shamrock Corp.

This formulation contains 4 lbs of active ingredient per gallon. It is a storage-stable suspension with complete, nonagglomerating dispersibility in water.

EXAMPLE 11

A mixed fungicide-insecticide composition is prepared as set forth in Example 10 above. This composition contains 20.5%, by weight each of tetrachloroisophthalonitrile fungicide and of 1-naphthyl-N-methylcarbamate insecticide. The concentration of total active ingredient in this composition is 4 lbs per gallon of formulation. The water-dispersibility of the composition is excellent, as is its suspension stability in storage.

It is to be understood that although the invention has been described with specific reference to particular embodiments thereof, it is not to be so limited, since changes and alterations therein may be made which are within the full intended scope of this invention as defined by the appended claims.

I claim:

1. A flowable, storage-stable, aqueous pesticide concentrate readily dilutable in water to provide an effective amount of pesticide for spray application which, prior to dilution, consists essentially of, by weight of the total concentrate,
    a. from 10 to 60% of an essentially water-insoluble pesticide component having an average particle size ranging between about 1 and 10 microns;
    b. from 1 to 10% of at least one nonionic surfactant; and
    c. from 0.02 to 1.0% of a heteropolysaccharide gum, the balance being water.

2. The composition of claim 1 wherein the nonionic surfactant is selected from the group consisting of alkylaryl polyether alcohols, alkyl polyether alcohols, polyoxyethylene fatty acid ethers, ethoxylated anhydrosorbitol esters, and ethoxylated polyoxypropylene glycols.

3. The composition of claim 2 wherein the nonionic surfactant is an alkylaryl polyether alcohol of the formula

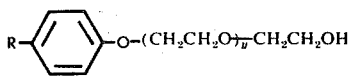

wherein R is a $C_8$-$C_{12}$ alkyl group and $y$ is an integer of 8–30.

4. The composition of claim 1 which contains, by weight of the total composition,
    a. from 40 to 60% of a water-insoluble pesticide component having an average particle size ranging from about 1 to 10 microns;
    b. from 3 to 7% of a nonionic surfactant;
    c. from 0.1 to 0.5% of heteropolysaccharide gum;
    d. from 0.5 to 2% of an anticaking agent;
    e. from 0.2 to 0.7% of an antifoaming agent;
    f. from 2 to 6% of a freeze-point depressant; and the balance, water.

5. The composition of claim 4 wherein the anticaking agent is an ultrafine, chemically inert essentially pure silica containing less than 5% moisture; the antifoaming agent is a silicone emulsion; and the freeze-point depressant is either ethylene or propylene glycol.

6. The composition of claim 1 wherein the essentially water-insoluble pesticide component is a fungicide.

7. The composition of claim 6 wherein the fungicide is tetrachloroisophthalonitrile.

8. The composition of claim 1 wherein the essentially water-insoluble pesticide component is a herbicide.

9. The composition of claim 8 wherein the herbicide is the dimethyl ester of tetrachloroterephthalic acid.

10. The composition of claim 1 wherein the essentially water-insoluble pesticide component is a mixture of a fungicide and an insecticide.

11. The composition of claim 10 wherein the fungicide is tetrachloroisophthalonitrile and the insecticide is N-methyl-1-naphthylcarbamate.

12. The composition of claim 1 which additionally contains from 0.2 to 10%, by weight, of an anticaking agent.

13. The composition of claim 1 which additionally contains from 0.1 to 5% of an antifoaming agent.

14. The composition of claim 1 which additionally contains from 1 to 10%, by weight, of a freeze-point depressant.

15. The composition of claim 1 which additionally contains, by weight, from 0.2 to 10% of an anticaking agent and from 0.1 to 5% of an antifoaming agent.

* * * * *

REEXAMINATION CERTIFICATE (381st)
United States Patent [19]
Marks

[11] B1 3,948,636
[45] Certificate Issued Sep. 10, 1985

[54] FLOWABLE AQUEOUS COMPOSITION OF WATER-INSOLUBLE PESTICIDE

[75] Inventor: Alfred F. Marks, Mentor, Ohio

[73] Assignee: SDS Biotech Corp., Del.

Reexamination Request:
No. 90/000,515, Mar. 2, 1984

Reexamination Certificate for:
Patent No.: 3,948,636
Issued: Apr. 6, 1976
Appl. No.: 305,064
Filed: Nov. 9, 1972

[51] Int. Cl.³ ............................................. A01N 25/22
[52] U.S. Cl. ..................................... 71/112; 71/79; 71/105; 71/DIG. 1; 514/782; 514/525; 514/478
[58] Field of Search ............ 71/79, 105, 112, DIG. 1; 514/782, 525

[56] References Cited
U.S. PATENT DOCUMENTS

| | | | |
|---|---|---|---|
| 2,786,011 | 3/1957 | Novak | 167/42 |
| 3,060,084 | 10/1962 | Littler | 167/42 |
| 3,717,452 | 2/1973 | Gibsen et al. | 71/117 |

*Primary Examiner*—Catherine L. Mills

[57] ABSTRACT

An easily handled, flowable, pesticide composition contains as essential components in water as the sole liquid medium, from 10 to 60%, by weight, of at least one solid, substantially water-insoluble pesticidally-active ingredient; from 1 to 10%, by weight, of a water-soluble nonionic surfactant; and from 0.02 to 1% by weight of a heteropolysaccharide gum. Optional ingredients of the composition include, for example, antifoam agents, anticaking agents, and freeze-point depressants. This composition is an extremely stable suspension. It is totally dispersible in water, providing agglomerate-free pesticidal spray compositions.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 4 are determined to be patentable as amended.

Claims 2, 3 and 5-15, dependent on an amended claim, are determined to be patentable.

1. A flowable, storage-stable, aqueous pesticide concentrate readily dilutable in water to provide an effective amount of pesticide for spray application which, prior to dilution, consists essentially of, by weight of the total concentrate,
   a. from 10 to 60% of an essentially water-insoluble pesticide component having an average particle size ranging between about 1 and 10 microns;
   b. from 1 to 10% of at least one nonionic surfactant; and
   c. from 0.02 to 1.0% of a [heteropolysaccharide] *xanthan* gum,
the balance being water.

4. The composition of claim 1 which contains, by weight of the total composition,
   a. from 40 to 60% of a water-insoluble pesticide component having an average particle size ranging from about 1 to 10 microns;
   b. from 3 to 7% of a nonionic surfactant;
   c. from 0.1 to 0.5% of [heteropolysaccharide] *xanthan* gum;
   d. from 0.5 to 2% of an anticaking agent;
   e. from 0.2 to 0.7% of an antifoaming agent;
   f. from 2 to 6% of a freeze-point depressant; and
the balance, water.

* * * * *